United States Patent [19]

Kaufhold

[11] Patent Number: 5,902,895
[45] Date of Patent: *May 11, 1999

[54] METHOD FOR THE CONTINUOUS PRODUCTION OF ESTERS OF THERMALLY UNSTABLE ACIDS

[75] Inventor: Manfred Kaufhold, Marl, Germany

[73] Assignee: Huels Aktiengesellschaft, Marl, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/851,070

[22] Filed: May 5, 1997

[30] Foreign Application Priority Data

May 4, 1996 [DE] Germany .............................. 196 17 991

[51] Int. Cl.$^6$ .................................................. C07C 255/03
[52] U.S. Cl. .......................... 558/441; 560/147; 560/186; 560/226; 558/440
[58] Field of Search .................................... 558/440, 441; 560/147, 226, 186

[56] References Cited

U.S. PATENT DOCUMENTS 5,637,761   6/1997   Miltenberger ............................ 560/226

FOREIGN PATENT DOCUMENTS 1 939 759   3/1970   Germany .

OTHER PUBLICATIONS

General College Chemistry by Keenan and Wood, pp. 250–254, 1971.
CA:88:169611, Abstract of Continuous esterification of substituted acetic acids with aliphatic alcohols, DD127117, Sep. 1977.
CA:106:175766, Abstract pf Synthesis and characterization of some cyanoacrylic esters, Rev Chim 37(3) 193–6, 1986.

*Primary Examiner*—Gary Geist
*Assistant Examiner*—Jean F. Vollano
*Attorney, Agent, or Firm*—Oblon, Spivak, McClelland, Maier & Neustadt, P.C.

[57] ABSTRACT

A method for the continuous production of esters of thermally unstable acids by the esterification, with or without a catalyst, of the acids with alcohols is provided. The method involves esterification at temperatures of approximately 80° C. to approximately 130° C., essentially in a single reaction zone, to which the acid and an excess of alcohol are continuously supplied and from which a vapor stream containing alcohol and water produced by the esterification reaction are removed, while at the same time removing an ester-rich liquid reaction mixture from the single reaction zone, from which the ester is obtained.

20 Claims, 2 Drawing Sheets

METHOD FOR THE CONTINUOUS PRODUCTION OF ESTERS OF THERMALLY UNSTABLE ACIDS

BACKGROUND OF THE INVENTION

1. Field of the Invention

The present invention relates to a method for the continuous production of esters of thermally unstable acids in essentially only one reaction zone in the liquid phase that is capable of providing high quantities of the esters.

2. Discussion of the Background

Various esters of thermally unstable acids are important intermediate products for the production of other valuable substances. For example, cyanoacetic acid esters are needed for the syntheses of heterocycles. 4-Chlorobutyric acid serves as a starting material for the synthesis of cyclopropane derivatives. A continuous esterification method is desired for the production of the needed technical quantities of these and other esters.

Gas phase esterification methods (see, for example, Ullmann, Encyclopedia of Technical Chemistry, 3rd Edition, 1967, Volume 18, p. 69) cannot be used because of the thermal sensitivity of the acids. DD 127 117 describes a continuous method that works in the liquid phase, wherein the acid is esterified in three successive stages in the presence of a catalyst—in the first stage in a cocurrent flow, in the second stage in a counterflow, and in the third stage, again in a counterflow. This method suffers from the following disadvantages: (1) it requires an additional entrainer for the removal of water generated during reaction, (2) it is expensive with regard to the apparatus used because of its three esterification stages, (3) it requires a considerable measurement and control technical outlay because of the different parameters in the three esterification stages, and (4) it tends to be otherwise troublesome to carry out.

In the production of cyanoacetic acid, the temperatures in the three esterification stages are 75° C. (column 4), 130° (column 1), and 110° C. (column 2), with conversions of 10 to 15%, 70 to 80% and 10 to 15%, respectively. This procedure takes into consideration the fact that cyanoacetic acid already begins to decompose beyond approximately 80° C. Accordingly, the temperature is increased step by step, and the end temperature of 100° is attained in a stage when only a small amount of unesterified cyanoacetic acid remains in the reaction mixture.

SUMMARY OF THE INVENTION

Accordingly one object of the present invention is to provide a process for the continuous production of esters of thermally unstable acids that provides high quantities of the esters in a simple one stage process.

A further object of the present invention is to provide a process for the continuous production of esters of thermally unstable acids that requires no additional entrainer for water produced during the esterification.

These and other objects of the present invention have been satisfied by the discovery of a process for the preparation of esters of thermally unstable acids comprising esterifying the acids with alcohols at a temperature of from approximately 80° C. to approximately 130° C. in a liquid phase, essentially in only one reaction zone, to which the acid and an excess of alcohol are continuously supplied and from which a vapor mixture of alcohol and the water generated during reaction, and a liquid reaction mixture rich in ester, are continuously drawn off and the ester is obtained from this.

BRIEF DESCRIPTION OF THE FIGURE

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
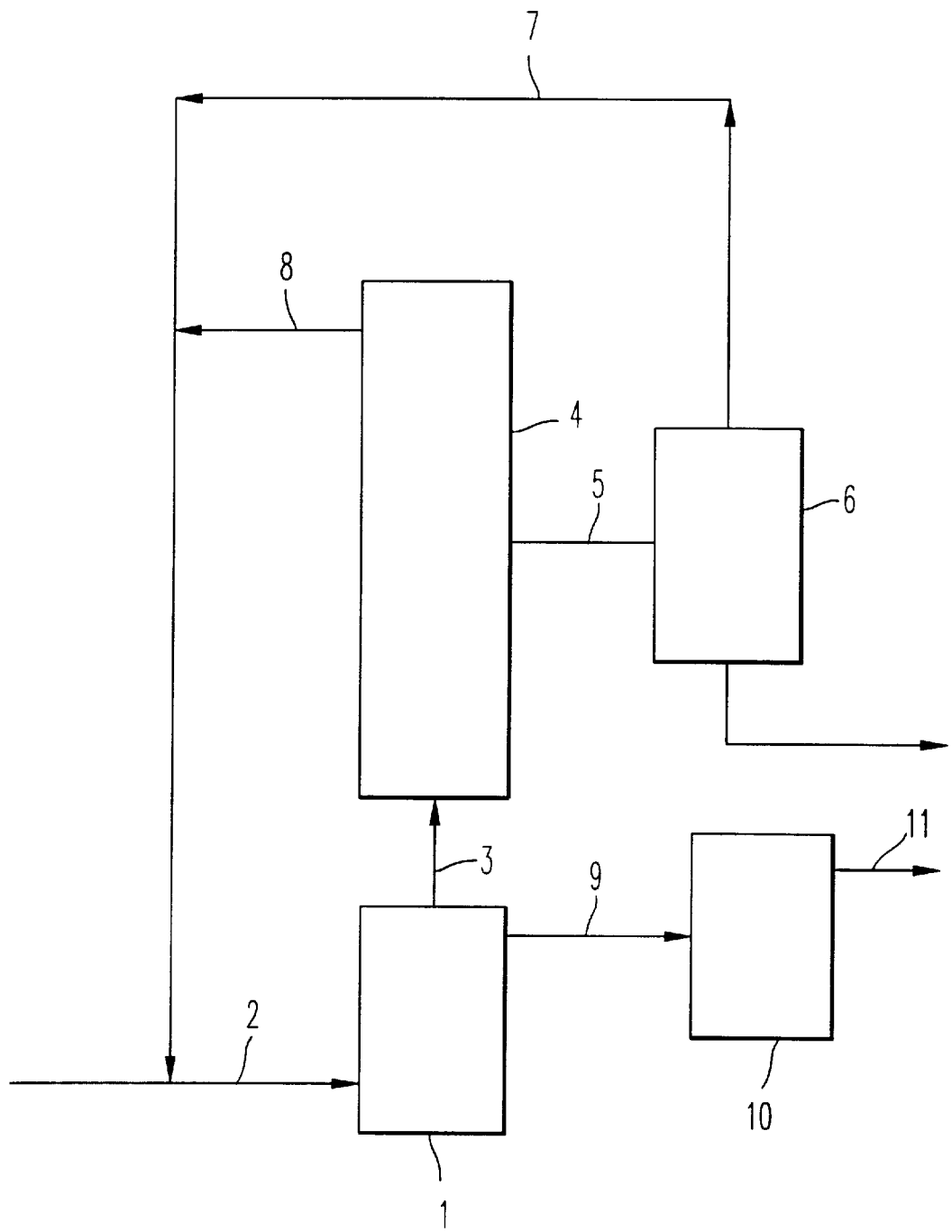
FIG. 1 provides a block diagram of an apparatus suitable for performing the method of the present invention.

Despite the relatively high temperatures and the considerable residence times of the thermally unstable acids in the reaction zone, the present method produces excellent yields of the pertinent esters. The method is relatively simple with respect to the apparatus, requires a smaller measurement and control technical outlay than the conventional continuous method and is therefore less liable to give trouble. Entrainers for the water generated during reaction or other auxiliaries are not needed.

As used herein, the term "thermally stable acids" denotes acids that decompose to a considerable extent at temperatures above approximately 150° C. Examples include, but are not limited to, cyanoacetic acid, 4-chlbrobutyric acid, thioglycolic acid, and malonic acid. Cyanoacetic acid can be esterified in a particularly advantageous manner according to the method of the present invention.

Alcohols for use in the esterification reaction of the present invention are preferably those that have a lower boiling point than the acid to be esterified. Suitable alcohols include alkanols with 1 to 3 carbon atoms—such as methanol, ethanol, —and isopropanol.

One important feature of the present invention is that the esterification is carried out in a liquid phase and, contrary to the method disclosed in DD 127 117, essentially in only one reaction zone. With the context of the present process, the term "essentially" means that the esterification can take place to a small extent, at another place outside the one reaction zone. As an example, a small amount of esterification can take place in the reflux of the column, by means of which alcohol and water are appropriately removed in vapor form. The acid to be esterified is also removed in the column in an amount in accordance with its vapor pressure, and in the reflux, which contains predominantly alcohol, can be esterified to a small extent. However, the predominant quantity (preferably greater than 90%, most preferably greater than 95%) of the ester is formed in the actual reaction zone.

The present esterification can be carried out with or without a conventional esterification catalyst. $C_{10}$–$C_{13}$ alkylbenzenesulfonic acids are particularly suitable as catalysts, because they can be metered well, are slightly soluble in the reaction mixture, and very effective. Other suitable esterification catalysts include sulfuric acid, alkanesulfonic acids (such as methane sulfonic acid), and p-toluenesulfonic acid. The esterification catalysts, when used, are appropriately used in quantities of approximately 0.1 to 1.0 wt %, with reference to the amount of thermally unstable acid used. The catalysts can be used individually or as a mixture of two or more.

The temperature in the reaction zone lies in the range of from approximately 80° C. to approximately 130° C., preferably from 80° C. to 120° C. The optimal temperature depends primarily on the acid used and whether the work is done with or without one or more esterification catalysts. The optimal temperature can be easily determined by routine experiments. By the joint use of a catalyst, acceptable space-time yields can be provided even at the lower temperatures in the range. For cyanoacetic acid with a catalyst, the optimal esterification temperature lies at from 100° C. to 120° C., preferably from 105° C. to 115° C. With 4-chlorobutyric acid without a catalyst, the optimal temperature is from 80° C. to 100° C. and preferably from 85° C. to 95° C.

The acid to be esterified, an excess of alcohol, and a catalyst, if desired, are continuously supplied to the reaction zone. The molar ratio of alcohol:acid is preferably 15:1 to 3:1, more preferably 10:1 to 4:1, and most preferably 8:1 to 5:1. Acid, alcohol, and catalyst (if desired) can be supplied individually, in combinations of two, or all together. In a preferred embodiment of the present method, the alcohol that is removed from the reaction zone along with the water generated by the reaction, is transferred back to the reaction zone after separation from the water. Depending on the geometry of the reaction zone, the aforementioned substances are preferably removed from the reaction zone as far as possible away from the site where the ester-rich liquid product is removed from the reaction zone. In this way, the fraction of unreacted acid in the ester-rich liquid product removed is minimized. The acid, the alcohol, and the catalyst (if present) can be introduced into the reaction zone at ambient temperature or preheated.

Excess alcohol and the water formed during reaction are continuously removed in vapor form from the reaction zone. The alcohols can form an azeotrope with water, as is the case with ethanol. Other alcohols, such as methanol, entrain water vapor, in accordance with the partial pressure of the water, over the reaction mixture. In both cases, it is appropriate to combine the continuous expulsion of the water with a likewise continuous reprocessing of the alcohol-water mixture, wherein the alcohol can be conducted back to the reaction zone, and the water is discarded. This can be done, for example, by introducing the vapor mixture into a column, from which practically pure alcohol (or its azeotrope with water) is removed at the head and the alcohol is conducted back to the reaction zone. At the same time, a water-rich lateral flow is drawn off, which can be reprocessed separately or also discarded, for example, by burning.

A liquid reaction product can be continuously drawn off from the reaction zone, that is rich in the formed ester and also contains unreacted acid and any higher-boiling secondary products, as well as alcohol, and small quantities of water. This liquid reaction product can be broken down into its components by distillation, and the desired ester can be obtained in high purity. This can occur batchwise or continuously. A suitable batch process involves first separating all volatile products from the nondistillable or practically nondistillable fractions, and then obtaining the ester from the volatile products by fractional distillation purification. With large product quantities, it is preferred to have continuous reprocessing.

The yield of desired ester can be increased even further and the content of acid in the end product can be further reduced by reesterifying the ester-rich liquid reaction mixture that is removed and/or obtained as a sump product before the purification distillation. To this end, the ester-rich liquid reaction product is dissolved in the alcohol, and the solution is once again subjected to the esterification conditions. By purification distillation of the resulting re-esterified product mixture, it is possible to produce highly pure, practically acid-free esters in good yields.

The present esterification and reesterification processes can be performed in conventional esterification apparatus. For example, a suitable vessel is one that has devices for regulated heating, for the regulated supply of the starting materials, for the regulated removal of the liquid reaction mixture, and for the maintenance and separation of the water and alcohol vapor mixture which leaves the vessel from above, as described above. Devices to thoroughly mix the esterification mixture, such as a blade mixer, are also preferred. Instead of a vessel, the present process can also be performed in a correspondingly equipped packed column, into which, for example, the acid to be esterified and perhaps the catalyst are introduced above, and the alcohol in the middle part, with the esterrich reaction product being removed in the lower part of the column. The column packings ensure a thorough mixing.

A block diagram of a suitable apparatus for the carrying out of the present method is represented in FIG. 1. In the lower part of the reactor 1, the acid to be esterified, the alcohol, and the catalyst (if desired) are introduced as a substance flow 2. The vapor flow 3 consisting essentially of alcohol and water vapor enters into the lower portion of column 4. A lateral flow 5 is provided for removal of a water-rich alcohol-water mixture from column 4. This mixture is reprocessed in continuous distillation 6 to alcohol 7, which is returned to the substance flow 2 along with the practically pure alcohol drawn off as a head flow 8 from column 4. The product flow 9 is removed from the upper part of the reaction and the desired ester 11 is obtained from it in the distillation 10.

Figure 2:
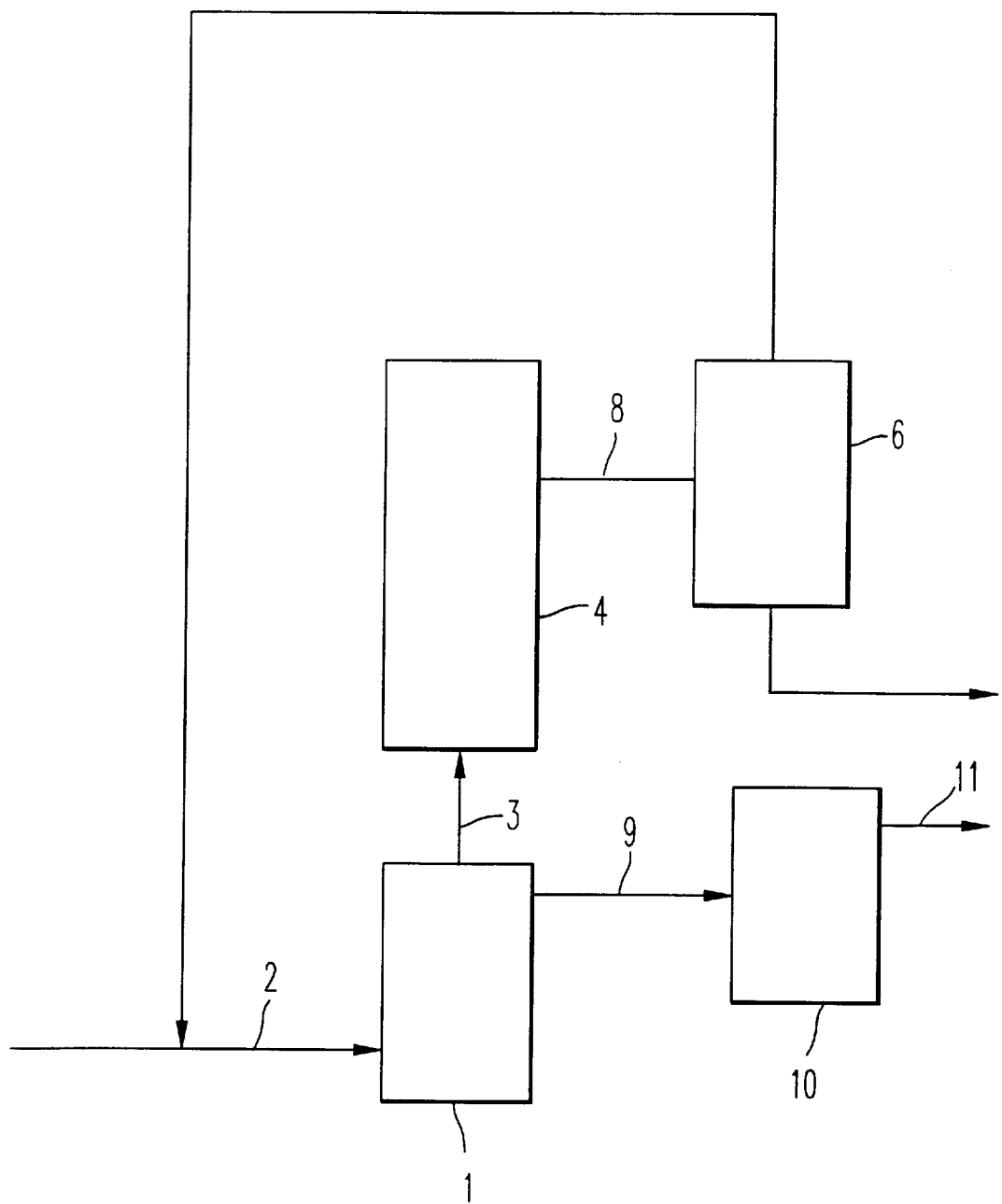
FIG. 2 provides a block diagram of an apparatus for performing a further embodiment within the method of the present invention.

A preferred, simplified variant of the arrangement according to FIG. 1 is given in FIG. 2. Only ester and acid are separated from alcohol and water in the correspondingly shorter column 4. The lateral flow 5 is omitted, and the head flow 8 is not returned directly to the substance flow 2, but rather is reprocessed to alcohol in column 6, and then returned to the substance flow 2.

EXAMPLES

Having generally described this invention, a further understanding can be obtained by reference to certain specific examples which are provided herein for purposes of illustration only and are not intended to be limiting unless otherwise specified. All percentages refer to weight % in the examples.

Example 1

Production of cyanoacetic acid methyl ester (MCYA)

The apparatus used corresponded to FIG. 1 and consisted of a double-walled, heatable glass flask with a capacity of 2 L (reactor 1)

an inlet tube for a mixture of cyanoacetic acid (CYA), methanol, and catalyst (substance flow 2), an immersion tube for the removal of the ester-rich reaction mixture (product flow 9), a stirrer, a 10 cm long lower and a 20 cm long upper column unit with Berl saddles as the filler (together column 4), a lateral removal port between the two column units for the removal of the water-rich alcohol-water mixture (lateral flow 5), alcohol removal (head flow 8) at the head of the column, a distillation bridge for the reprocessing of the removed reaction mixture 9 (distillation part 10).

1.1 Production of an esterification mixture

The following substances were placed in the glass flask: 1,417.9 g (16.7 mol) of cyanoacetic acid (CYA), 535.1 g (16.7 mol) of methanol, and 6 g of $C_{10}$–$C_{13}$ alkylbenzenesulfonic acid (Marlon®-AS3).

The mixture was heated to 110° C. within 1 h. Then, only methanol (160 g/h) was metered in for the preparation of a steady-state esterification mixture for 7 h. At the head of column 4, head flow 8 was drawn off, and between the column units, the lateral flow 5 was drawn off. The reflux ratio (quantity removed:quantity flowing back) was regulated at 2:1. The temperature at the head removal was 63 to 64° C., and the temperature at the lateral flow removal 5 between the column units rose from 76° C. to 86° C. within 7 h. The reaction mixture (product flow 9) was not yet removed. Within 7 h, the following were obtained: 385 g of head flow with 1.3% water, 599 g of lateral flow with 37.0% water.

The reaction mixture in the glass flask contained the following after 7 h, according to a gas chromatographic analysis (GC): 81.4% cyanoacetic acid methyl ester (MCYA) 10.8% cyanoacetic acid 1.8% water 5.1% methanol 1.2 Esterification phase For the balance of the materials, the esterification phase was subdivided into cycles of 7 h each. In the first cycle, cyanoacetic acid, methanol, and catalyst (substance flow 2) were metered in from the very beginning, and 1 h later, removal of the reaction mixture (product flow 9) began. The quantities of both substance flow 2 and product flow 9 were regulated in such a way that the level of the reaction mixture in reactor 1 remained constant. During the first 2 h after the beginning of the metering of substance flow 2, the reflux ratio was set at 1:1 and subsequently increased to 2:1. The temperature at the head was unchanged (63 to 64° C.); the temperature at the lateral removal between the column units (lateral flow 5) was 68 to 70° C.

In the following cycles, the reaction mixture (product flow 9) was removed from the very beginning, and the reflux ratio was 2:1 throughout. Moreover, the conditions were the same as before.

Within each individual cycle of 7 h, 1,285 g of a mixture formed by mixing the following:

510 g (6.0 mol) of cyanoacetic acid,
1,153 g (36 mol) of methanol, and
2 g (approximately 0.4 wt %, based on CYA) of Marlon®-AS3, were supplied to reactor 1.

The following were removed in the individual cycles:

|  | Amount in g removed Cycle No. | | | | |
| --- | --- | --- | --- | --- | --- |
| Product | 1 | 2 | 3 | 4 | 5 |
| Head flow | 360 | 373 | 327 | 397 | 445 |
| Lateral flow | 470 | 460 | 505 | 431 | 424 |
| Product flow | 333 | 395 | 447 | 446 | 501 |

The weight loss was only approximately 0.6%. The content of MCYA in the lateral flow 5 was only 0.1%; with the water content at 12–15%. On the other hand, the head flow contained 8.97% methanol and was returned to the esterification with the substance flow 2. The gas chromatographic analysis (GC) of the removed reaction mixture (product flow 9) produced the following values:

|  | Cycle No. | | | | |
| --- | --- | --- | --- | --- | --- |
| Product (%) | 1 | 2 | 3 | 4 | 5 |
| Water | 1.2 | 1.0 | 1.0 | 1.1 | 1.1 |
| Methanol | 4.9 | 5.2 | 5.4 | 5.3 | 5.2 |
| MCYA | 83.6 | 84.1 | 83.6 | 83.4 | 83.8 |
| CYA | 9.2 | 8.4 | 8.5 | 8.7 | 8.1 |
| MDME* | 0.6 | 0.8 | 1.0 | 1.1 | 1.3 |
| Acetonitrile | 0.4 | 0.3 | 0.3 | 0.3 | 0.4 |

*Malonic acid dimethyl ester

One can see that the values, particularly those for the desired product MCYA, were practically constant. The conversion of the cyanoacetic acid was approximately 90%.

1,150 g of the ester-rich reaction mixture (product flow 9) removed in the various cycles were skimmed into two fractions of high boilers at a distillation bridge. The mass balance was as follows:

| Fraction No. | Temperature, °C. | | Pressure, mbar | Wt., g | Wt., % |
| --- | --- | --- | --- | --- | --- |
|  | Sump | Head |  |  |  |
| 1 | 60–86 | 40–47 | 199–150 | 70 | 6.1 |
| 2 | 68–84 | 68–67 | <1 | 974 | 84.9 |
|  |  |  | — | 103 | 9.0 |

Based on the measured acid number (AN) of 438, the residue had a CYA content of 66.4%.

Fractions 1 and 2 gave the following compositions according to GC:

| Component, % | Fraction 1 | Fraction 2 |
| --- | --- | --- |
| Methanol | 63.4 | 0.01 |
| Water | 18.2 | 0.04 |
| Acetonitrile | 7.6 | ca. 0.1 |
| MDME | 0.5 | ca. 1.3 |
| MCA | 9.6 | ca. 98.1 |
| CYA (from AN) | 0.1 | ca. 0.5 |

The yield of MCYA (98% purity) was 87.8%. By means of fractional distillation, it was possible to obtain MCYA with a purity of 99.7%.

Example 2

4-Chlorobutyric acid methyl ester (CBME)

Crude 4-chlorobutyric acid (CBA) was produced, in a known manner, by introducing gaseous hydrogen chloride into γ-butyrolactone (BL), at 100° C., until hydrogen chloride was no longer taken up. Subsequently, nitrogen was passed through the reaction mixture, in order to expel excess hydrogen chloride. The acid number was then 393. 1,818 g crude CBA was obtained from 1,373 g (15.8 mol) of BL.

The crude CBA was diluted with methanol in a molar ratio of methanol:CBA of 6:1—that is, with 3,037 g methanol (solution 1). For the esterification, 2,211 g of solution 1 were used, corresponding to approximately 7.2 mol of BL. For the esterification, the apparatus described in Example 1 and corresponding to FIG. 1 was used, but with a 1-L glass flask as the reactor.

2.1 Production of an esterification mixture 300 g of solution 1 were placed in the reactor. The pressure was lowered to 500 mbar, and solution 1 was heated at reflux to boiling. Within 5 h, another 456 g of solution 1 were metered in. The temperature in the reaction mixture rose, in this time, from 54 to 72° C. One hour after the start of metering, removal at the head (head flow 8) and between the column units (lateral flow 5) was started, wherein a reflux ratio of 5:1 was established. The quantity removed as lateral flow 5 was regulated by a control valve. The following were obtained within the time period of 5 h:

234 g of head flow 8 having 0.44% water 143 g of lateral flow 5 having 2.04% water 2.2 Esterification phase The balance of the materials was determined for two cycles. In the first cycle, 825 g of solution 1 were metered in within 7 h. A head flow 8 and, between the column units, a lateral flow 5 were removed from the very beginning; with a reflux ratio of 2.5:1. After 5 h, the temperature in the reaction mixture rose from 72° C. to 92° C. At this time, the removal of the reaction mixture (product flow 9) was started. The following were obtained within 7 h:

201.4 g head flow 8 with 1.0% water 299.7 g lateral flow 5 with 18.1% water 32.6 g product flow 9

In the second cycle, 630 g of solution 1 were metered in within 5 h. The reflux ratio continued to be 2.5:1 and the temperature in the reaction mixture was 88 to 92° C. The reaction mixture (product flow 9) was removed from the very beginning. Within 5 h, the following were obtained:

115 g head flow 8 with 0.4% water 240 g lateral flow 5 with 11% water 83 g product flow 9

After 5 h, the esterification was ended. 805 g of the reaction mixture (sump product) remained in reactor 1.

In total, 2,211 g solution were used. 2,140 g were recovered. The loss accordingly was 3.2%.

The various flows and products had the following composition according to GC:

| Component | Head flow 8 | Lateral flow 5 | Product flow 9 | Sump product |
| --- | --- | --- | --- | --- |
| Methanol | 99.4 | 83.2 | 5.2 | 2.6 |
| Water | 0.5 | 12.7 | 2.4 | 1.2 |
| CBME | <0.1 | 4.0 | 70.3 | 74.8 |
| CBA | — | <0.1 | 4.3 | 3.2 |
| BL | <0.1 | <0.1 | 8.0 | 9.4 |

The table shows that the reaction water was practically completely contained in lateral flow 5 and practically pure methanol was obtained as head flow 8.

2.3 Reesterification

For further reduction of the content of CBA, the product from product flow 9 and the sump product were combined (862 g crude ester) and, together, reesterified. The crude ester had the following composition (%) according to GC:

| | |
| --- | --- |
| Methanol | 12.8 |
| Water | 1.2 |
| CBME | 73.6 |
| CBA | 3.5 |
| BL | 9.2 |

The crude ester was diluted with an equal quantity of methanol (to give solution 2) and used for the reesterification. To this end, 400 g of solution 2 were poured into the reactor in the first reesterification cycle, a pressure of 500 mbar was established, and solution 2 was heated at reflux. Within 6 h, 793 g of solution 2 were metered in. The removal of the product at the head (head flow 8) and between the column units (lateral flow 5), with a reflux ratio of 2.5:1, was immediately started. The reaction mixture (product flow 9) was not yet removed. Within 6 h, the following were obtained:

256 g head flow 8 with 0.2% water 351 g lateral flow 5 with 2.1% water

In the second reesterification cycle, 578 g solution 2 were metered in within 4.5 h. The temperature in the reaction mixture was 92° C. and the reflux ratio was again 2.5:1. The removal of the reaction mixture (product flow 9) was immediately started. The following were obtained during 4.5 h:

73 g of head flow 8 having 0.3% water 179 g of lateral flow 5 having 3.2% water 104 g of product flow 9

When reesterification was ended, 779 g of reaction mixture (sump product) remained in the reactor.

In total, 1,742 g of product were recovered as various flows and as the sump product. 1,771 g of solution 2 were used. The loss was 1.6%.

The products from the various flows (both cycles combined) and from the sump had the following composition:

| Component | Head flow 8 | Lateral flow 5 | Product flow 9 | Sump product |
| --- | --- | --- | --- | --- |
| Methanol | 99.7 | 97.6 | 3.7 | 2.8 |
| Water | 0.1 | 2.0 | 0.5 | 0.4 |
| CBME | <0.1 | 0.3 | 78.1 | 80.1 |
| CBA | — | — | 0.6 | 0.5 |
| BL | <0.1 | <0.1 | 8.9 | 9.4 |

It was possible to lower the contents of CBA and water in the product flow 9 and in the sump product to <1% by means of the reesterification.

2.4 Purification distillation

Product flow 9 and the sump product were combined (883 g). 853 g of this mixture were used for purification distillation by means of a 0.5-m-long distillation column filled with Berl saddles (4×4 mm). 4 fractions were removed:

| Fraction No. | Temperature, °C. Sump | Head | Pressure | Weight | Reflux ratio |
| --- | --- | --- | --- | --- | --- |
| 1 | 81–115 | 38–107 | 133 | 9 | 20:1 |
| 2 | 115–125 144 | 108–110 | 133 | 632 | 5:1 20:1 |
| 3 | 145–147 | 115–131 | 133 | 37 | 20:1 |
| 4 | 154–229 | 135–130 | 133 | 83 | 5:1 |
| Residue | | | | 53 | |
| Cooling trap | | | | 22 | |

The fractions had the following compositions:

| | Fractions | | | |
| --- | --- | --- | --- | --- |
| Component | 1 | 2 | 3 | 4 |
| Methanol | 2.3 | <0.1 | <0.1 | <0.1 |
| Water | 2.4 | <0.1 | <0.1 | <0.1 |
| CBME | 84.9 | 98.4 | 81.9 | 6.2 |

-continued

| Component | Fractions | | | |
|---|---|---|---|---|
| | 1 | 2 | 3 | 4 |
| CBA | 8.4 | <0.1 | <0.1 | <0.1 |
| BL | 0.3 | 1.5 | 17.5 | 93.5 |

Fraction 3 did not contain any interfering impurities and could be used again in the next distillation. Therefore, the quantity of CBME contained in this fraction was taken into consideration in the yield calculation. The yield of CBME (from fractions 2 and 3) was then 71% of the theoretical, based on BL used. With fraction 4, usable BL was again recovered. The yield of CBME was 82% of the theoretical, based on consumed BL.

This application is based on German Patent Application 196 17 991.2, filed with the German Patent Office on May 4, 1996, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters: Patent of the United States is:

1. A method for the continuous production of esters of thermally unstable acids, comprising:
   supplying a thermally unstable acid selected from the group consisting of cyanoacetic acid, 4-chlorobutyric acid, thioglycolic acid and malonic acid and an excess of an alcohol continuously to a reactor having essentially a single reaction zone,
   wherein during said esterifying step, a vapor stream consisting essentially of said alcohol and water generated during said esterifying step is continuously removed from said reactor and wherein an ester-rich liquid reaction mixture containing therein said ester is continuously removed from said reactor, wherein said ester is obtained from said ester-rich liquid reaction mixture.

2. The method according to claim 1, wherein the thermally unstable acid and alcohol are supplied together to the single reaction zone at a site in the single reaction zone which is remote from a second site where the ester-rich liquid reaction mixture zone is removed from the single reaction zone.

3. The method according to claim 1, further comprising the steps of continuously:
   transporting the vapor stream a lower portion of a first separation column;
   removing, from a middle portion of said first separation column, a water-rich liquid mixture;
   separating said water-rich liquid mixture, in a second separation column, into said alcohol and water;
   transporting said alcohol from said separating step back to said single reaction zone;
   removing from an upper portion of said first separation column, an approximately pure stream of said alcohol; and
   returning said approximately pure stream of said alcohol back to said single reaction zone.

4. The method according to claim 1, further comprising the steps of continuously:
   transporting said vapor stream to a lower portion of a first separation column;
   removing, from an upper portion of said first separation column, a liquid mixture comprising said alcohol and water;
   separating said liquid mixture in a second separation column into separate streams of water and said alcohol; and
   returning said separate stream of said alcohol to said single reaction zone.

5. The method according to claim 1, wherein the ester is obtained from said ester-rich liquid reaction mixture by distillation.

6. The method according to claim 1, wherein said alcohol is an alkanol with 1 to 3 carbon atoms.

7. The method according to claim 1, wherein said thermally unstable acid is cyanoacetic acid, and the temperature in the single reaction zone is from 100 to 120° C.

8. The method according to claim 7, wherein said temperature in the single reaction zone is from 105 to 115° C.

9. The method according to claim 1, wherein said thermally unstable acid is 4-chlorobutyric acid, and the temperature in the single reaction zone is from 80 to 100° C.

10. The method according to claim 9, wherein said temperature in the single reaction zone is from 85 to 95° C.

11. The method according to claim 1, wherein said alcohol and said thermally unstable acid are present in a molar ratio of alcohol:thermally unstable acid of from 15:1 to 3:1.

12. The method according to claim 11, wherein said molar ratio of alcohol:thermally unstable acid is from 10:1 to 4:1.

13. The method according to claim 12, wherein said molar ratio of alcohol:thermally unstable acid is from 8:1 to 5:1.

14. The method according to claim 1, wherein said ester-rich liquid reaction mixture is transported back to said single reaction zone for reesterification.

15. The method according to claim 1, wherein an esterification catalyst is added in said supplying step.

16. The method according to claim 15, wherein said esterification catalyst is added in an amount of from 0.1 to 1.0 wt %.

17. The method according to claim 15, wherein said esterification catalyst is a $C_{10}$–$C_{13}$ alkylbenzenesulfonic acid.

18. The method according to claim 1, wherein said thermally unstable acid is a member selected from the group consisting of thioglycolic acid and malonic acid.

19. The method according to claim 1, wherein less than 10% by weight of the ester is produced by esterification outside of said single reaction zone.

20. The method according to claim 19, wherein less than 5% by weight of the ester is produced by esterification outside of said single reaction zone.

* * * * *